United States Patent [19]

Wyss et al.

[11] 4,148,321

[45] Apr. 10, 1979

[54] APPARATUSES AND METHODS FOR THERAPEUTIC TREATMENT AND ACTIVE MASSAGES OF MUSCLES

[76] Inventors: Oscar A. M. Wyss, Physiologisches Institut, Raemistrasse 69, 8006 Zuerich; Aurio dit Giovanni Monti, 107a, Rte. de Grand-Lancy, 1212 Grand-Lancy, Geneva, both of Switzerland

[21] Appl. No.: 721,491

[22] Filed: Sep. 8, 1976

Related U.S. Application Data

[63] Continuation-in-part of Ser. No. 526,970, Nov. 25, 1974, abandoned.

[30] Foreign Application Priority Data

Nov. 26, 1973 [CH] Switzerland .................... 16588/73

[51] Int. Cl.² ............................................. A61N 1/36
[52] U.S. Cl. ............................................... 128/420 A
[58] Field of Search ....................... 128/420 A, 420 R

[56] References Cited

U.S. PATENT DOCUMENTS

| | | | |
|---|---|---|---|
| 2,434,497 | 1/1948 | Kearsley | 128/421 |
| 3,096,768 | 7/1963 | Griffith, Jr. | 128/420 A |
| 3,626,926 | 12/1971 | Kuzin et al. | 128/420 A |
| 3,774,620 | 11/1973 | Hansjurgens | 128/420 A |
| 3,895,639 | 7/1975 | Rodler | 128/422 |

FOREIGN PATENT DOCUMENTS

| | | | |
|---|---|---|---|
| 1109280 | 6/1961 | Fed. Rep. of Germany | 128/420 A |
| 467502 | 6/1937 | United Kingdom | 128/420 A |

*Primary Examiner*—William E. Kamm
*Attorney, Agent, or Firm*—Stevens, Davis, Miller & Mosher

[57] ABSTRACT

Apparatus and method for the treatment and active massage of muscles, the apparatus comprising a generator arrangement providing a modulated alternating current with a medium-frequency carrier having a frequency comprised between 3000 Hz and 100,000 Hz, and an adjustable low modulating frequency of a fraction of 1 Hz, preferably both the carrier and the modulating currents being sinusoidal. Directly or after optional conversion to a polyphase current, a variable modulated current is supplied to electrodes placed about a body portion, e.g. a limb, whereby the current is made to flow transversally through the muscles, producing painless rhythmic muscular contractions.

6 Claims, 7 Drawing Figures

APPARATUSES AND METHODS FOR THERAPEUTIC TREATMENT AND ACTIVE MASSAGES OF MUSCLES

This is a continuation-in-part of the applicants' earlier patent application Ser. No. 526,970, filed Nov. 25, 1974, titled "Apparatus for the Treatment and Active Massage of Muscles", now abandoned.

The invention relates to an apparatus and a method for the treatment and active massage of muscles.

It should be noted that in the present application, the words "treating" and "treatment" do not intend to relate to the medical meaning of this word, such as in the sense of "caring for a patient" or a part of his or her body, or of "seeking cure or relief of a disease", but they relate to "handling, managing, dealing with" (namely the body of a person or parts thereof), or to "subjecting the same to some action" or to "process for improvement", such as appearance, well-being, cleanliness, etc.

It has already been sought to provide treatment and active massage of human muscles by means of electric currents. The use of direct, so-called galvanic currents, either continuous or intermittent, has been proposed, but this has the drawback of causing painful contractions of the muslces, despite which the method is still used.

Rectified or non-rectified alternating currents with a low frequency of the order of 50 to 100 Hz have also been tried, but they may involve tetanization which is unpleasant for the treated person and makes the method unsuitable. Tetanization is characterized by chronic spasms of the voluntary muscles of the human body similar to the muscular tetanus, which is an acute infectious disease.

The use of alternating currents at medium frequency (according to physiologists' terminology, essentially between 3000 and 100,000 Hz) does not cause painful sensations. On the contrary, it causes permanent, painless contractures. The effect is analogous to that of non-intermittent direct currents with, however, the advantage of not producing unpleasant sensations. However, permanent contractures are not suitable for the treatment and active massage of the muscles.

The use of high-frequency alternating currents (again, according to physiologists' terminology, above 100,000 Hz) simply causes heating of the tissues (called diathermy) but causes neither contractions nor pain. It is thus likewise unsuitable for therapeutic treatment of the muscles.

For the re-education of the muscles, i.e. in order to produce active massage, the muscles must work regularly, that is to say, contract and relax periodically at a very low frequency, such as a fraction of one cycle or 1 Hz. Up until now, it has been impossible to provoke such working of the muscles without pain by means of electrical currents. Indeed, the use of direct currents, as we have seen, is unsuitable because painful; the use of alternating currents at low frequencies is likewise unsuitable because painful; the use of alternating currents at medium frequency is also unsuitable because it does not provoke periodical contractions of the muscles.

The inventors have overcome this apparent impossibility of creating a therapeutic treatment of the muscles by means of electrical currents, by combining the simultaneous use of (physiologically) medium-frequency alternating currents and low-frequency alternating currents, in that the former are modulated by means of the latter. As claimed herein, a practical range has been established for the medium frequency, between 3000 and 100,000 Hz, the most efficient frequencies being between 5000 and 20,000 Hz. As for the low frequency, the preferred practical frequency has been found of the order of a fraction of 1 Hz.

The inventors have thus obtained the surprising effect that, due to the presence of the medium-frequency carrier current, the modulation in amplitude by means of the low-frequency current allows rhythmical contractions to be obtained at the frequency of the modulating current, without producing any disagreeable sensations for the patient.

In other words, the fact that a medium-frequency carrier current is used eliminates the painful effect which would be felt if the low-frequency current were applied alone. This painful effect disappears when the low-frequency current is applied for modulating the carrier current. This unexpected and surprising effect had never been noticed until the present inventors conceived the invention.

It is admitted that conventional designations of "low", "medium" and "high frequencies" in electronics do not exactly coincide with the ranges used herein, according to the physiologists' determinations. Among physiologists, the generally accepted medium frequency range runs between 3000 Hz and 100,000 Hz (see for example Takao Kumazava: Excitation of muscle fibre membrane by means of transversely applied middle-frequency current pulse, in Helvetica Physiologica et Pharmacologica Acta, 26, 1969, p. 257).

The explanation of the paradox of the above-explained unexpected and surprising effect of the present invention is the following: an alternating current at (physiologically) medium frequency produces a permanent contraction of the muscles as soon as the maximum amplitude exceeds a certain limit. By modulating a medium-frequency carrier current at a very low frequency, the amplitude of the modulated medium-frequency current is made to vary periodically to the rhythm of the low-frequency modulation. The rate of modulation is selected so that the amplitude of the modulated current varies periodically between values respectively lower and higher than the threshold. The result is a rhythmical contraction of the muscles at the very low frequency. Since the low-frequency current does not act as such on the muscle, the treatment is painless. It is the medium frequency which produces the contractions (again, in a painless manner), and the modulation gives (similarly painlessly) a rhythm to these contractions. By varying the low frequency of the modulating current, the rhythm of the contractions is varied.

Another observation on which the invention is based is that the modulated current does not produce unpleasant effects when the carrier current, and also preferably the modulating current is sinusoidal, i.e. it is exempt from harmonic distortions and abrupt variations which would be liable to produce painful effects.

It has also been observed that the treatment may be further improved by using, instead of a monophase modulated current, a polyphase current modulated in the same way, preferably a triphase current. The use of a polyphase current offers the advantage that it permits a deeper action on the muscles than monophase current which latter tends to concentrate its action along the shortest path.

It is also the object of the present invention to provide the aforesaid apparatus to promote general well-being, remove fatigue from human muscles, which apparatus can in some instances also be considered a substitute for physical exercise.

It is the object of the invention to provide an apparatus and a method for the treatment and active massage of muscles while avoiding tetanization or other effects which cause pain.

The apparatus according to the invention is characterized in that it comprises generator means providing a modulated alternating current that includes a carrier current with a frequency between 3000 and 100,000 Hz, and a current for modulating the carrier current, the modulator current having a frequency of the order of a fraction of 1 Hz, at least the carrier current of the two currents being sinusoidal, at the exclusion of intermittent frequency effects, and at least two electrodes for supplying the resulting variable modulated current to a body portion wherein muscles are to be treated, in placing the electrodes on the surface of and in contact with the skin, whereby the resulting modulated current flows transversally through and acts deeply on the muscles, and produces painless rhythmic muscular contractions.

The method according to the invention is characterized by essentially comprising the steps of: generating a modulated alternating current that includes a carrier current with a frequency between 3000 Hz and 100,000 Hz, and a modulator current having a frequency of the order of a fraction of 1 Hz; modulating the carrier current with the modulator current wherein at least the carrier current of the two currents is sinusoidal, leading the resulting modulated current to at least two electrodes adapted to be associated with a body portion wherein the muscles are to be treated; placing the electrodes on the surface of and in contact with the skin of the body portion; and thereby inducing a transversal flow of the resulting modulated current through the muscles, acting deeply thereon, and producing painless rhythmic muscular contractions that treat and massage those muscles, at the exclusion of intermittent frequency effects being applied to the body portion.

Other objects and many of the attendant advantages of the invention will be readily appreciated as the same becomes better understood by reference to the following detailed description, when considered with the accompanying drawings which shows, by way of an example, an exemplary embodiment of the treating and massaging apparatus according to the invention, and an explanation of the inventive method. Both will be described simultaneously.

Figure 1:
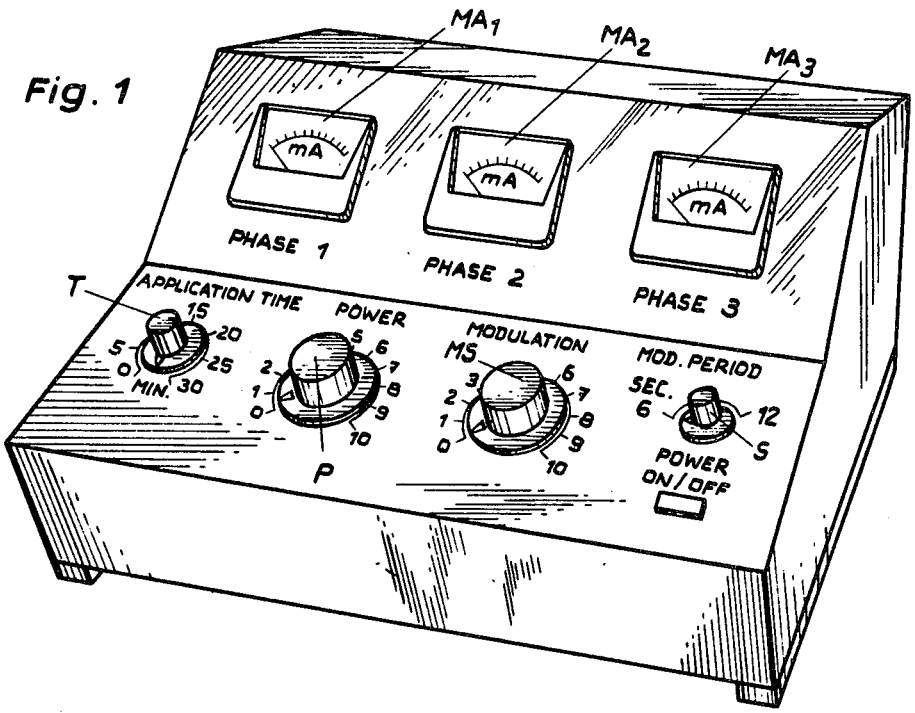
FIG. 1 is an external view of an embodiment of the apparatus according to the invention, the input current of which is an alternating monophase current, whereas its output is a modulated triphase current as explained hereinafter.
Figure 2:
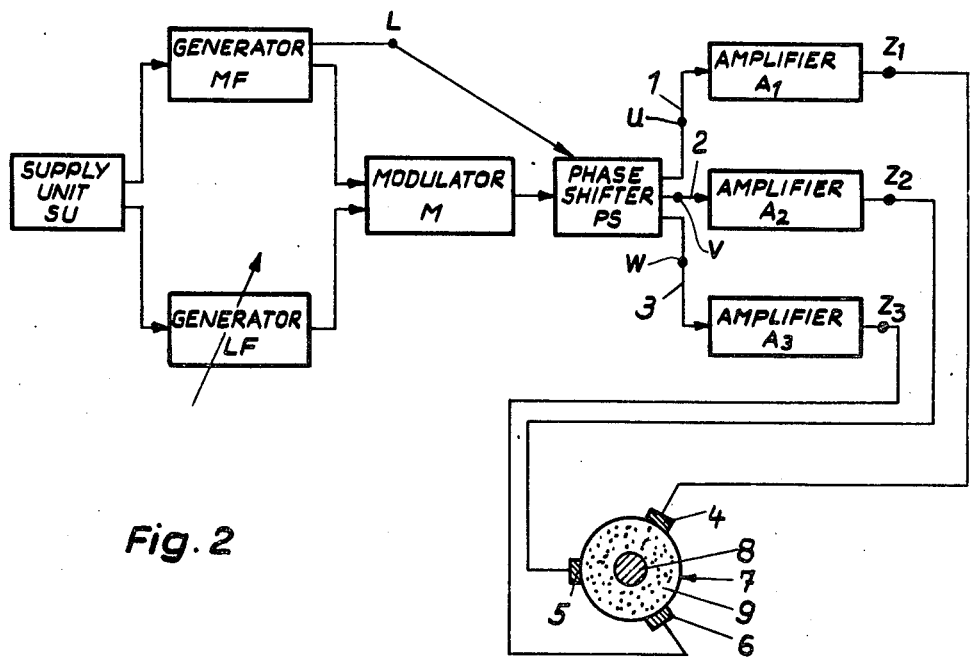
FIG. 2 is a block diagram showing the different units of the apparatus according to FIG. 1.

Referring to FIGS. 1 and 2, the apparatus comprises a power supply unit designated SU, a conventional generator MF providing a sinusoidal alternating carrier current of a sufficiently high frequency as not to be painful, for example between 3000 and 100,000 Hz, preferably between 3000 and 20,000 Hz, and a generator LF providing a sinusoidal low-frequency alternating modulating current at a frequency for example of the order of 1/5 to 1/10 Hz. The current delivered by generator MF is a carrier current, and that delivered by generator LF is a modulating current that serves to modulate the carrier current. Generator LF is preferably adjustable both in amperage and frequency, as schematically indicated.

Modulation of the current delivered by generator MF by the output current of generator LF is performed in a modulator M which is preferably arranged in a known manner to enable adjustment of the degree of modulation.

The monophase output current of modulator M is optionally delivered to a phase shifter PS transforming it into a triphase current modulated in the same manner. The three phases are designated by numerals 1, 2 and 3 and delivered to respective amplifiers $A_1$, $A_2$ and $A_3$ whose lead-outs are connected to respective electrodes 4, 5 and 6.

These electrodes are shown applied to a human limb 7, for example an arm, whose bone is schematically shown at 8 and a muscular part at 9.

The three electrodes 4, 5, 6 are angularly spaced apart, preferably symmetrically, about the limb 7 being treated. It can readily be appreciated that the use of a triphase current permits a deep and fairly uniform action of the current on the muscles 9 of the arm. It can also be seen from the drawing that the electrodes 4, 5, 6 are placed about and in contact with the limb 7 so that the modulated current flows transversally through the muscles 9.

In order that the invention be fully understood, the wiring of the various units, shown diagrammatically in FIG. 2, is shown in detail in FIGS. 3 to 6, and the apparatus itself is illustrated in FIG. 1 to wich reference will be had later.

The wiring diagrams of FIGS. 3 to 6 are conventional. Explanations will be given to the extent necessary for a good understanding of the invention.

Figure 3:
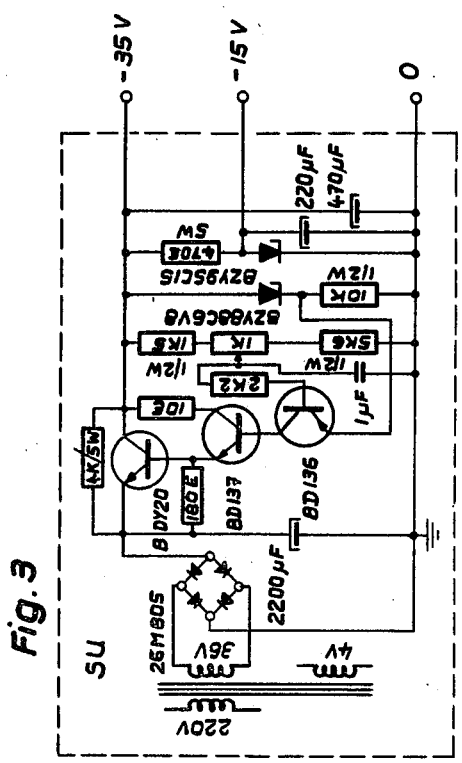
FIG. 3 is a wiring diagram of a power supply unit (SU)

Power Supply Unit SU (FIG. 3)

This is a conventional supply, itself supplied with monophase alternating current and providing a d.c. voltage of −15 V and −35 V in relation to ground 0.

Three stabilisation transistors BD 136, BD 137 and BDY20 provide direct current amplification (e.g. a Darlington circuit). The polarization of the transistor BD136 is controlled by a Zener diode BZY88C6V8. A potentiometer 1K permits the maximum output voltage to be fixed at −35 V in relation to the ground O. A condenser 470μF between the −35 V and the ground serves to improve the filtering of the −35 V. A zener diode BZY95C15 allows the obtention of a stable voltage of −15 V in relation to the ground O. A condenser 220μF between the −15 V and the O serves to improve the filtering of the −15 V. A condenser 1μF between the cursor of the potentiometer 1K and the ground serves to reduce the residual undulation voltage. A resistor 10K between the anode of the zener diode BZY88C6V8 and the ground O has been selected so that the output current discharged by the power supply unit SU is limited to 2.5 amperes. Thus a short-circuit between the O and the −35 V cannot cause any damage, since the transistor BD 136 will be blocked. Thus no current will circulate in the power transistor BDY20.

Only a low current will pass through a resistor 4K/5W used to provide the necessary current for the diode BZY88C6V8 at the time of switching on.

Figure 4:
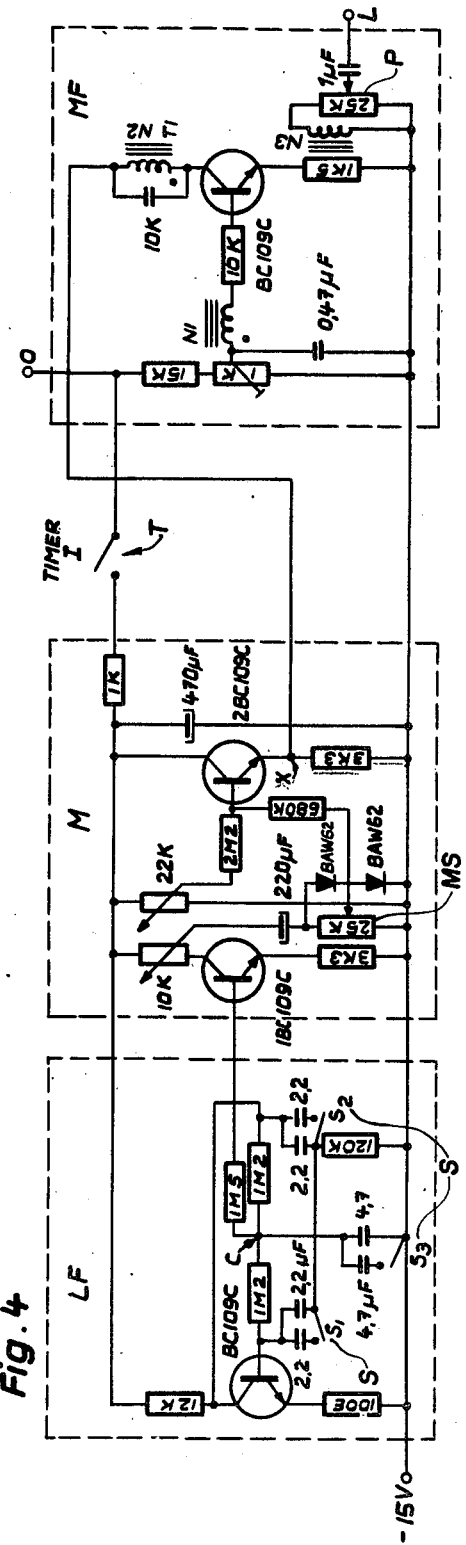
FIG. 4 is a wiring diagram of a low-frequency alternating modulating current unit (LF), a modulator (M) and a medium frequency generator unit (MF), also in FIG. 2.

Low-frequency alternating modulating current unit LF (FIG. 4)

This is a conventional generator of sinusoidal current the frequency of which is, in the example shown, optionally of either 1/5 Hz (1 period = 12 seconds) or 1/10 Hz (1 period = = 6 seconds). The choice between these two frequencies is made by means of a switch button S having two positions and which actuates simultaneously three switches S1, S2, S3 (FIG. 4). The open positions of these switches correspond to deactivation of one of each of pairs of condensers 2,2µF and 4,7µF. The closed positions correspond to the parallel connection of the two condensers in each pair. In the example, one of the positions (12 sec.) corresponds to a frequency of 1/5 Hz and the other (6 sec.) to a frequency of 1/10 Hz, as was just explained (see the respective positions of the switch S in FIG. 1.

A transistor BC109C, which has an amplification coefficient of at least 500, oscillates in double T mode and gives a choice of one of the two frequencies in question.

The low-frequency alternating sinusoidal current generated by the LF unit serves, as will be seen further on, to modulate a carrier current at medium frequency.

Modulator unit M (FIG. 4)

The sinusoidal voltage at low frequency generated by the unit LF is drawn off at a point C of this unit (FIG. 4) and applied to the base of a transistor 1BC109C of the unit M through a resistor 1M5. This transistor serves as an impedance changer.

A variable resistor 10K serves to adjust the maximum of the modulation rate. A variable resistor 22K serves to polarize a second transistor 2BC109C which is a modulator. A potentiometer 25K which is actuated by a switch MS (ten positions being indentified in FIG. 1) serves to regulate, as desired, the modulation rate up to a maximum fixed by the resistor 10K.

When the cursor of the switch MS or potentiometer 25K reaches the potential −15 V, one adjusts the polarization of the base of the transistor 2BC109C by means of the variable resistor 22K so as to obtain a direct current of about 1 V between a point X and the −15 V. By moving the cursor of MS away from the −15 V, a voltage varying according to the rhythm of the LF oscillation is obtained on the base of the transistor 2BC109C, which produces a synchronous variation of the voltage at the point X, which determines the modulation, as will be seen when the unit MF is described hereinafter.

Medium-frequency generator unit MF (FIG. 4)

This generator is a conventional LC oscillator generating a sinusoidal current having a frequency between 3000 Hz and 20,000 Hz. In the example under consideration, this frequency is of 11,000 Hz. This current is intended for modulation by the low frequency current generated by the unit LF; it is thus the carrier current.

The transistor BC109C of unit MF performs as a reaction oscillator with modulation by the collector. T1 is a transformer comprising three coils N1, N2, N3.

The supply voltage of the collector of this transistor is provided by the point X of the unit M. The amplitude of the alternating medium-frequency voltage is thus a function of the instantaneous voltage at the point X.

A cursor of a potentiometer 25K of MF is actuated by a switch P (see the positions 1 to 10 in FIG. 1) and serves to regulate the output voltage of the modulated current, i.e. of the output power.

The potentiometer 25K of M, actuated by the switch MS of FIG. 1, serves, as already stated, to regulate the modulation rate. When its cursor is at −15 V, the generator MF produces a frequency of 11,000 unmodulated Hz at the potentiometer 25K (switch P) of MF. By moving the cursor away from the point −15 V, a variable sinusoidal voltage at the frequency of LF is obtained at X, and this produces the modulation. The modulation rate is regulated by a potentiometer 25K of M (switch MS), as already stated.

I is a switch between units M and MF controlled by a timer the control button T of which is shown in FIG. 1. It serves to regulate as desired the duration of the patient's treatment by means of the apparatus. A resistor 1K and the condenser 470µF of M, inserted after the switch I, produce a time constant which causes the voltage to vary slowly at X when switched on and off in order to avoid shocks to the patient.

Figure 5:
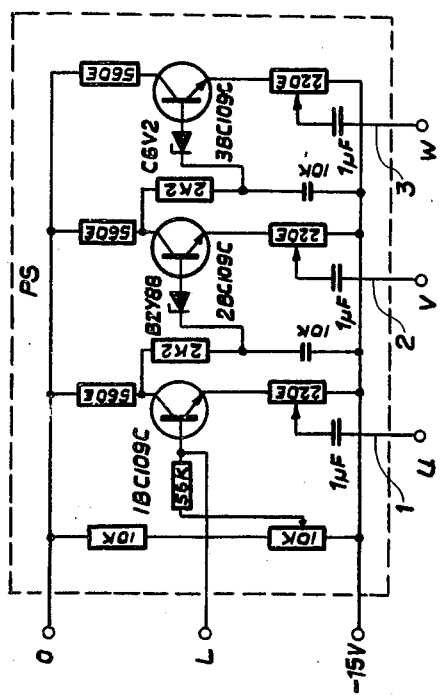
FIG. 5 is a wiring diagram of a phase shifter (PS) converting the monophase output modulated current of the MF unit into a triphase modulated current.

Phase shifter unit PS (FIG. 5)

This is a phase converter changing the monophase modulated current into a three-phase modulated current (of the same frequency and modulated in the same manner as the monophase current provided by the unit MF of FIG. 4).

A first of three transistors, 1BC109C, receives through an input L the modulated control voltage of a point L of the output of MF, thus through the switch P or potentiometer 25K (of MF) and a condenser 1µF (both of MF).

At an output terminal U, i.e. at a cursor of a first potentiometer 220 E, placed between the emitter of this first transistor and the −35 V, a voltage is obtained which is in phase with that of 11,000 Hz generated by MF and modulated by the low frequency of LF.

A second transistor, 2BC109C provides at a terminal V a voltage identical to that provided at U by the first transistor, but with a lead of 120° relative ro the voltage at U. This dephasing takes place through a phase-shift network constituted by a resistor 2K2 and a condenser 10K. A Zener diode BZY88 serves to supply the polarization to the transistor 2BC109C.

A third transistor, 3BC109C, provides at a terminal W a voltage which is identical to that of V but with a lead of 120° in relation thereto. A phase-shift network is identical to that of the second transistor, as may be seen in FIG. 5. The circuits leading to the terminals V and W are substantially identical with that described for U.

The three potentiometers 220 E are adjusted once and for all in order to balance the voltages of the three phases.

Figure 6:
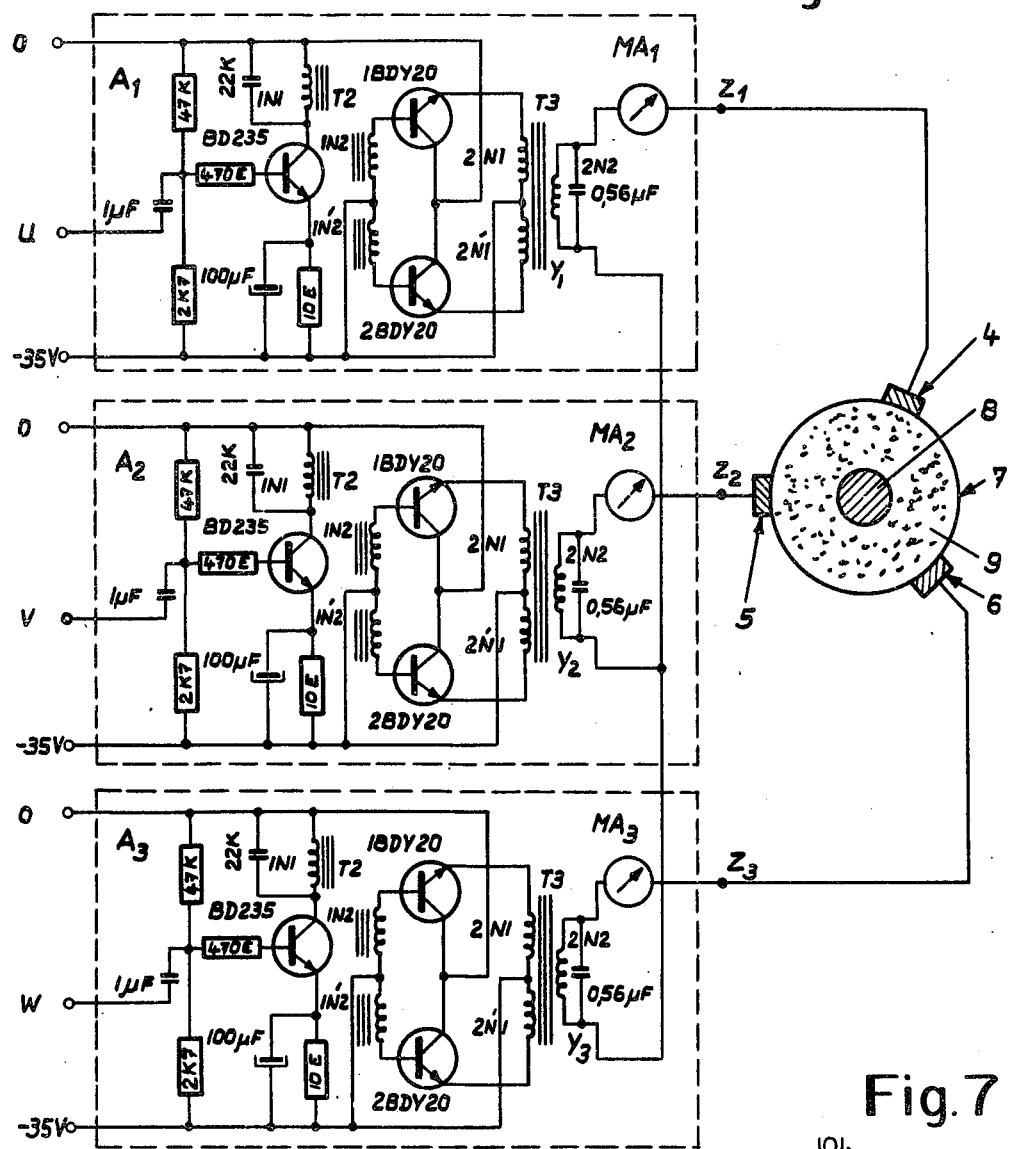
FIG. 6 is a wiring diagram of three amplifiers $A_1$, $A_2$, $A_3$ in FIG. 2, amplifying the output three-phase currents of unit PS.

Amplifying units A1, A2, A3 (FIG. 6)

Since the voltages at U, V and W (FIG. 5) are low, it is necessary to amplify them respectively by means of amplifying phase units A1, A2 and A3. These three units are identical as may be seen in FIG. 6. Hence only one of them will be described. The respective inputs U, V, W correspond to the output terminals of unit PS.

A transistor BD235 is a preamplifier. Between its collector and the ground O, a transformer T2 is inserted comprising a primary coils reactor 1N1 and two identical secondary coil 1N2, 1N'2 connected to the bases of two output transistors 1BDY20 and 2BDY20. The emitters of these transistors are connected to two identical primary coils 2N1 and 2N'1 of a transformer T3, one of the ends of the secondary 2N2 of which leads to a phase output terminal Z1 of the unit A1 (terminals Z2, Z3 for A2 and A3, respectively) by means of a milliamperemeter M1 (and similar meters M2, M3) which latter also appear in FIG. 1.

The other end of this secondary, Y1, is connected to corresponding outputs Y2, Y3 of the two other phases in units A2, A3. It may be seen that this is a star-connected circuit.

On the bottom part of FIG. 6, the right-hand side of FIG. 2 has been repeated, to make for easier understanding.

Electrodes 4 to 6 are placed on the limb at a location sufficiently distant from motory points or muscles of the body. FIG. 1 illustrates a preferred, exemplary embodiment of the inventive apparatus with the various controls that have been described so far in connection with the FIGS. 4 and 6. The three instruments identified by M1, M2 and M3 are the milliammeters for measuring the intensity of the respective phases of the variable modulated current that is being applied to the patient during the treatment; they also appear within the circuits of the respective amplifiers A1, A2 and A3 of FIG. 6. Control T identifies the knob of the timer that is set by hand to the chosen time of application of the apparatus to the patient, also appearing in FIG. 4 between the units M and MF. Element P is the knob for adjusting the intensity of the current being applied, the electric circuitry being shown at the right-hand end of FIG. 4, within unit MF. Control MS in FIG. 1 is the knob for adjusting the degree of modulation of the output current, as shown in the circuit of unit M that forms part of FIG. 4. Finally, S is the knob for adjusting the period, in seconds, of the modulating current, namely 6 or 12 seconds, as was explained. A conventional push-button marked "POWER ON/OFF" is also shown underneath the knob S, for energizing and disconnecting the apparatus; this may correspond, for example, to a simple switch or interrupter in the primary 220V input of the unit SU in FIG. 3.

Figure 7:
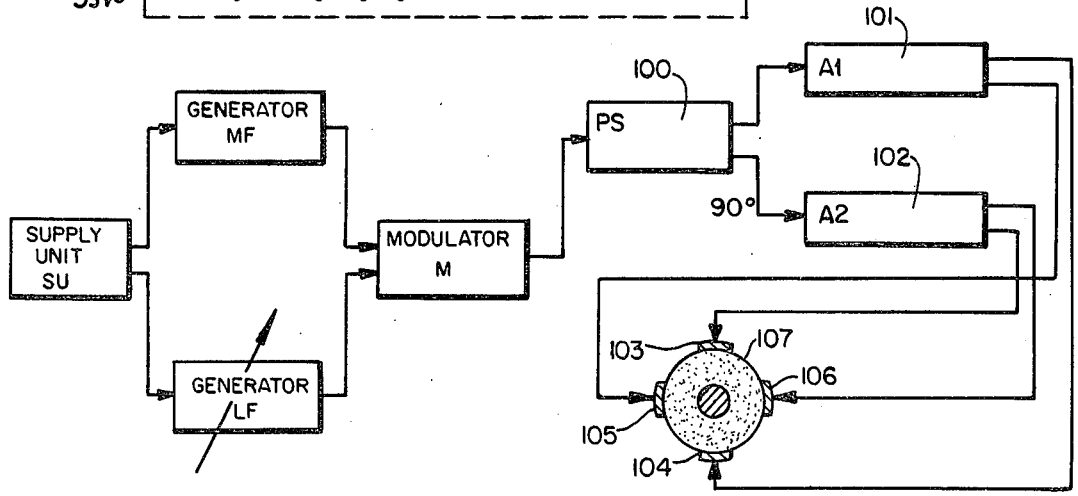
FIG. 7 is a block diagram of a second embodiment of the invention employing a 90° phase shifter.

As a variation, a modified phase shifter providing a bi-phase current can be used to supply four application electrodes disposed in principle at 90° to another. Referring to FIG. 7, there is shown a 90° phase shifter 100 for dividing the output of the modulator M into two components 90° out of phase with each other. These components are coupled through amplifiers 101 and 102 to electrodes 103 to 106 which are angularly spaced apart, preferably symetrically as shown, about the limb 107 being treated, the output of amplifier 101 being coupled across electrodes 105 and 106 and the output of amplifier 102 being coupled across electrodes 103 and 104.

As another variation, it might be possible to apply the modulated monophase current, namely the output of unit M, directly to a single electrode; this is suitable in cases where it is not essential to have a large distribution of current in a plane transverse to the muscles. It will be understood that with only one electrode being applied, ground is used to constitute the other electrode.

Use of the inventive apparatus and method has shown in practice that it can absolutely produce painless rhythmic muscular contractions at a variable frequency; this is exactly what one has to date sought to obtain for the treatment and active massage of muscles, and for enhancing general well-being. As has been mentioned in the introduction, intermittent or impulse-type currents are avoided in the present invention, which cause painful sensations and unpleasant effects. Experience has shown that impulse-type stimulation of muscles and body portions results in synchronized excitatory effects that are liable to become very painful.

The described apparatus enables the production of rhythmic contractions at the frequency of the modulating current, these contractions being painless because the modulated current (which alone acts on the muscles) is a current of sufficiently high frequency, and hence painless. Only the amplitude of this high-frequency current varies according to the modulation, and this does not produce tetanization if the carrier and modulating currents are sinusoidal.

Although the preceding description has been concerned with the treatment of the muscles of limbs of the human body, it is clear that muscles of other parts of the body may be treated in a similar manner and with the same advantages.

It should be understood, of course, that the foregoing disclosure relates only to preferred embodiments of the inventive apparatus and method, and that it is intended to cover all changes and modifications of the example described which do not constitute departures from the spirit and scope of the invention.

What we claim is:

1. An apparatus for treating and actively massaging muscles, comprising
    first generator means for generating a sinusoidal carrier current having a frequency in the range of 3000 to 100,000 Hz,
    second generator means for generating a modulating current having a frequency of less than one Hz,
    modulator means coupled to said first and second generator means, said modulator means amplitude modulating said carrier current with said modulating current,
    at least three electrodes for application to a portion of the body wherein muscles are to be treated, and
    phase shifting means for coupling the output of said modulator means to said at least three electrodes, the application of said amplitude modulated current to the body producing without pain rhythmical contraction of the muscles at said frequency of less than one Hz.

2. The apparatus defined by claim 1 wherein said phase shifting means provides a three-phase output voltage and wherein three electrodes are provided for symetrical disposition about the body portion to be treated, the currents through said three electrodes being displaced 120 degrees in time phase with respect to each other.

3. The apparatus defined in claim 1 wherein said phase shifting means provides a two-phase output voltage and wherein four electrodes are provided for symetrical disposition about the body portion to be treated, the currents through said four electrodes being displaced 90 degrees in time phase with respect to each other.

4. The apparatus defined by claim 1 wherein said carrier current has a frequency in the range 5000 to 20,000 Hz and said modulating current has a frequency from about 0.1 to 0.2 Hz.

5. The method of treating and actively massaging muscles comprising the steps of generating a sinusoidal carrier current having a frequency in the range 3000 to 100,000 Hz, generating a modulating current having a frequency of less than one Hz, modulating said carrier current with said modulating current to produce an amplitude modulated current, phase shifting said amplitude modulated current, and applying said phase shifted amplitude modulated current to at least three electrodes applied to a portion of the body wherein muscles are to be treated, the application of said amplitude modulated current to said body producing without pain rhythmical contraction of the muscles at said frequency of less than one Hz.

6. The method defined by claim 5 wherein said carrier current has a frequency in the range 5000 to 20,000 Hz and said modulating current has a frequency from about 0.1 to 0.2 Hz.

* * * * *